United States Patent [19]

Esmon et al.

[11] Patent Number: 5,336,610
[45] Date of Patent: Aug. 9, 1994

[54] METHOD FOR PURIFICATION OF THE ZYMOGEN OF PROTEIN C OR THE HEAVY CHAIN THEREOF USING MONOCLONAL ANTIBODY HPC-4

[75] Inventors: Charles T. Esmon; Naomi L. Esmon, both of Oklahoma City, Okla.

[73] Assignee: Oklahoma Medical Research Foundation, Oklahoma City, Okla.

[21] Appl. No.: 982,832

[22] Filed: Nov. 30, 1992

Related U.S. Application Data

[60] Division of Ser. No. 730,040, Jul. 12, 1991, Pat. No. 5,202,253, which is a continuation of Ser. No. 292,447, Dec. 30, 1988, abandoned.

[51] Int. Cl.$^5$ ............................ C12N 9/48; C07K 3/20; C07K 15/28
[52] U.S. Cl. .................................... 435/212; 530/380; 530/381; 530/413; 530/388.25; 435/240.27; 435/172.2; 435/70.21
[58] Field of Search ............... 530/388.25, 413, 380, 530/381; 435/240.27, 172.2, 70.21, 212

[56] References Cited

PUBLICATIONS

Nakamura, S., "Immunoaffinity purification of protein C by using conformation-specific monoclonal antibodies to protein C-calcium ion complex" *Biochimica et Biophysica Acta*, 925, 85-93 (1987).

Primary Examiner—Paula K. Hutzell
Attorney, Agent, or Firm—Kilpatrick & Cody

[57] ABSTRACT

A $Ca^{2+}$ dependent monoclonal antibody that specifically binds to a specific twelve peptide sequence (E D Q V D P R L I D G K) in the activation region of the Protein C. The antibody does not bind to Activated Protein C and can be used to inhibit activation of Protein C by thrombin-thrombomodulin. The antibody can be isolated from cell culture or ascites fluid in large quantities by affinity chromatography with mild conditions using the peptide bound to an immobilized substrate.

The antibody has a number of specific uses in isolation and characterization of Protein C and as a model for the design of $Ca^{2+}$ dependent antibodies for the isolation of other proteins, as a diagnostic, and as a therapeutic to prevent activation of Protein C. The Protein C can be naturally produced or produced by expression of the recombinant gene. Advantages of the antibody in purification of Protein C include the specificity for Protein C and not Activated Protein C, and the unique $Ca^{2+}$-peptide binding specificity which allows the binding site to be protected when it is being immobilized on the chromatographic support. In vivo, the antibody has been demonstrated to inhibit tumor growth. The antibody can also be used to promote clotting in patients having high levels of Factor VIII inhibitors.

2 Claims, 2 Drawing Sheets

METHOD FOR PURIFICATION OF THE ZYMOGEN OF PROTEIN C OR THE HEAVY CHAIN THEREOF USING MONOCLONAL ANTIBODY HPC-4

This is a divisional of pending prior application Ser. No. 07/730,040 filed on Jul. 12, 1991, issued as U.S. Pat. No. 5,202,253 on Apr. 13, 1993, which is a continuation of U.S. Ser. No. 07/292,447 filed on Dec. 30, 1988, now abandoned.

BACKGROUND OF THE INVENTION

This invention is generally in the area of antibodies to plasma proteins, specifically Protein C, and methods for use thereof.

Protein C is a vitamin K-dependent plasma protein zymogen to a serine protease. Upon activation it becomes a potent anticoagulant. Activated protein C acts through the specific proteolysis of the procoagulant cofactors, Factor VIIIa and Factor Va. This activity requires the presence of another vitamin K-dependent protein, protein S, calcium and a phospholipid (presumably cellular) surface. Referring to FIG. 1, from *Hemostasis and Thrombosis: Basic Principles and Clinical Practice* 2nd Ed., Colman, R. W., et al., p. 236(J. B. Lippincott, Philadelphia, Pa. 1987), protein C circulates in a two-chain form, with the larger, heavy chain bound to the smaller light chain through a single disulfide link. A small proportion of the protein also circulates in a single chain form, where a lys-arg dipeptide in the molecule connects the light chain directly to the heavy chain. Protein C is activated to activated protein C (APC). Thrombin is capable of activating protein C by the specific cleavage of the $Arg^{12}$-$Leu^{13}$ bond in the heavy chain. In vivo, in the presence of physiological concentrations of calcium, the rate of this activation is enhanced dramatically when thrombin is bound to the endothelial cell cofactor, thrombomodulin. Matschiner, et al., *Current Advances in Vitamin K Research*, pp. 135-140, John W. Suttie, ed. (Elsevier Science Publishing Co., Inc. 1988) have further reviewed the role of the Vitamin K dependent proteins in coagulation.

Protein C has been shown to have major importance in vivo. Patients deficient in protein C, or its cofactor, protein S, show pronounced thrombotic tendencies. Babies born totally deficient in protein C exhibit massive disseminated intravascular coagulation (DIC) and a necrotic syndrome which leads to death within the first few weeks of life if untreated. Activated protein C has also been shown to protect animals against the coagulopathic and lethal effects of endotoxin shock, as described by Taylor, et al., in *J. Clin. Invest.* 79, 918-925 (1987).

As first reported by Kisiel, in *J. Clin. Invest.* 64, 761-769 (1979), Protein C was originally isolated in semi-pure form from plasma using classic protein purification techniques, including barium citrate adsorption and elution, ammonium sulfate fractionation, DEAE-Sephadex chromatography, dextran sulfate agarose chromatography, and preparative polyacrylamide gel electrophoresis. This procedure was vastly improved and facilitated by the discovery of a unique antibody to Protein C, designated HPC-4, described by Stearns, et al., in *J. Biol Chem.* 263(2), 826-832 (1988). As detailed by Esmon, et al., at the Joint IABS/CSL Symposium on Standardization in Blood Fractionation including Coagulation Factors, Melbourne, Australia 1986 (reported in *Develop. biol. Standard.*, 67, 51-57 (S. Karger, Basel, 1987), Protein C can be isolated from human plasma by batch adsorption of diluted heparinized plasma on QAE Sephadex, washing with buffered 0.15M NaCl and eluting with 0.5M NaCl, recalcifying and batch adsorbing with HPC-4, then washing with a $Ca^{2+}$ containing buffer and eluting the Protein C with an EDTA containing buffer.

HPC-4 is a calcium-dependent monoclonal antibody to human protein C. The epitope recognized by the antibody has been identified and corresponds to the stretch of amino acids in the zymogen of protein C which spans the thrombin cleavage site. Activated protein C is not recognized by HPC-4.

Several antibodies to human protein C have been reported, for example, by Laurell, et al., *FEBS Letts.* 191(1), 75-81 (1985); Wakabayashi, et al., *J. Biol. Chem.* 261, 11097-11105 (1986); Sugo, et al., *Thromb. Hemost. Abstrs., Brussells,* 229 (1987); and Ohlin, et al., *J. Biol Chem.* 262, 13798-13804 (1988). Some of these are calcium dependent, for example, one of the antibodies reported by Laurell, et al. However, as far as can be determined in the published reports, this dependence is due to the requirement for calcium binding to the light chain of protein C and the antibodies recognize epitopes on the light chain. Other antibodies recognize the region around the thrombin cleavage site on the heavy chain, but these are not calcium dependent, including the HPC-4 described by Ohlin, et al. The HPC-4 antibody of Ohlin, et al., is not both $Ca^{2+}$ dependent and directed against the activation region, and is therefore different from the antibody of the present invention.

None of the other antibodies that bind to the $Ca^{2+}$ binding region of Protein C recognize only Protein C and not the activated form, Situations may arise in which the protein uncontaminated by its active form is desirable. This is particularly the case with reference to therapeutic uses of the antibody to inhibit Protein C activation.

Unfortunately, although the use of the antibody of the present invention, and, more recently, the properties, have been reported in the literature, it has not been publicly available for use in isolation, diagnostic, or therapeutic methodologies.

It is therefore an object of the present invention to provide a $Ca^{2+}$ dependent antibody which binds to the activation region of Protein C.

It is a further object of the present invention to provide a method and means for using a domain of this $Ca^{2+}$ dependent antibody for isolation of other non-metal binding peptides or proteins by metal dependent affinity chromatography.

It is a still further object of the present invention to provide a method and means for using this $Ca^{2+}$ dependent antibody for therapeutic purposes.

It is yet another object of the present invention to provide this $Ca^{2+}$ dependent antibody, antibodies, derivatives and conjugates thereof, for diagnostic purposes.

SUMMARY OF THE INVENTION

A $Ca^{2+}$ dependent monoclonal antibody that specifically binds to a specific twelve peptide sequence (E D Q V D P R L I D G K) in the activation region of the Protein C of non-bovine origin, including human, pig, baboon, and canine Protein C. The antibody does not bind to Activated Protein C and can be used to inhibit activation of Protein C by thrombin-thrombomodulin.

The antibody can be isolated from cell culture or ascites fluid in large quantities by affinity chromatography using the peptide sequence described above bound to an immobilized substrate.

The antibody has a number of specific uses in isolation and characterization of Protein C, as a diagnostic, and as a therapeutic to prevent activation of Protein C. The Protein C can be naturally produced or produced by expression of the recombinant gene. Advantages of the antibody in purification of Protein C include the specificity for Protein C and not Activated Protein C, and the ability to protect the antigen binding site of the antibody with the defined epitope peptide and calcium during immobilization of the antibody to the chromatographic support. In vivo, the antibody has been demonstrated to inhibit tumor growth. Further, the antibody, Protein S antibodies, C4B binding protein, alone or in combination, can be effective in promoting clotting in patients having high levels of Factor VIII inhibitors, hemophilia, platelet deficiencies (thrombocytopenia), and other clotting disorders where it is desirable to increase clotting. In addition, the use of the defined epitope for the large scale purification of the antibody and the stability of the antibody to viral inactivation procedures have not been disclosed previously.

DETAILED DESCRIPTION OF THE INVENTION

Figure 1:
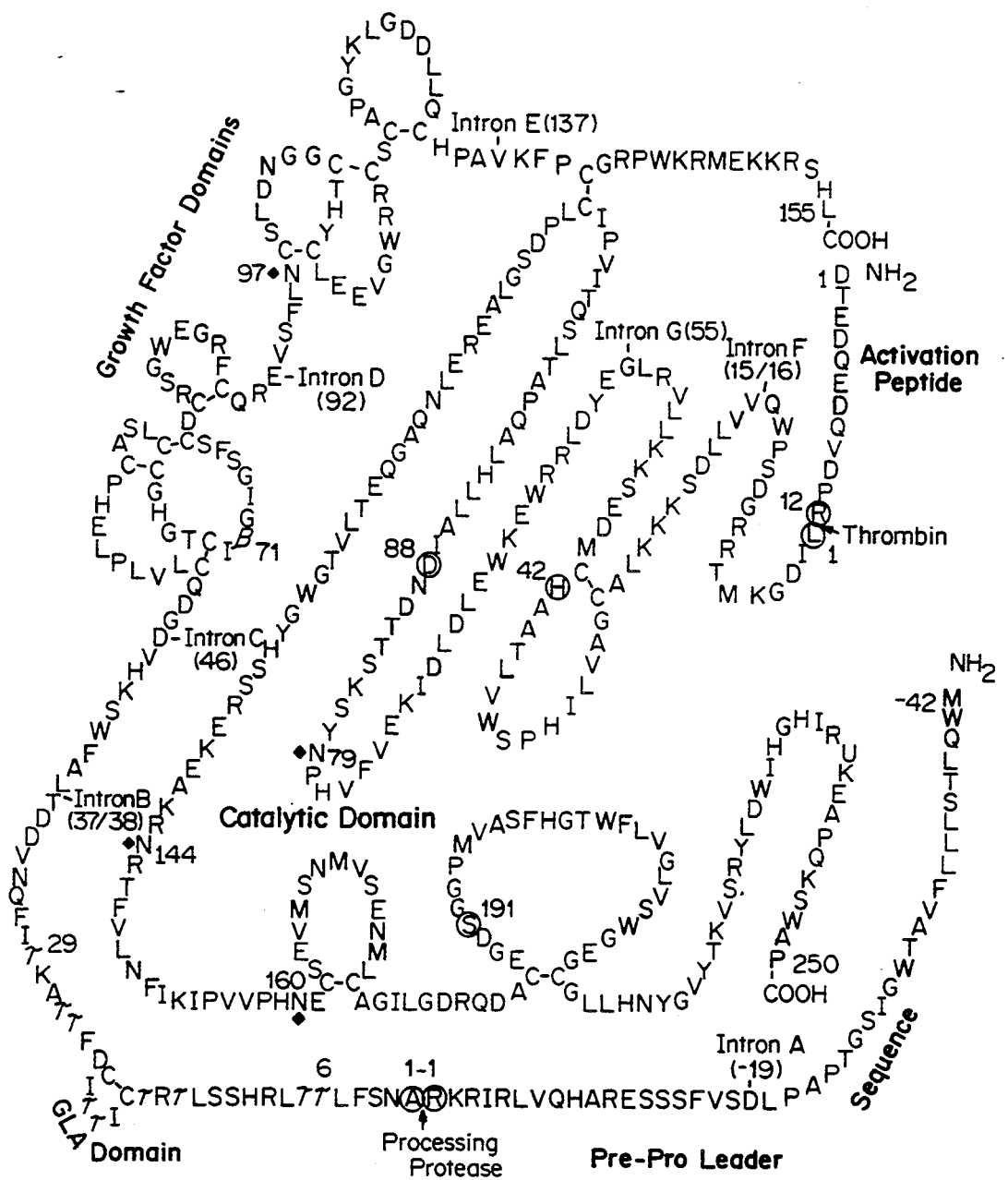
FIG. 1 is a schematic of Protein C showing the heavy and light chains bound by a single disulfide bond, and designating the Gla-region, the growth factor-like region, the serine protease region, and the activation peptide region.
Figure 2:
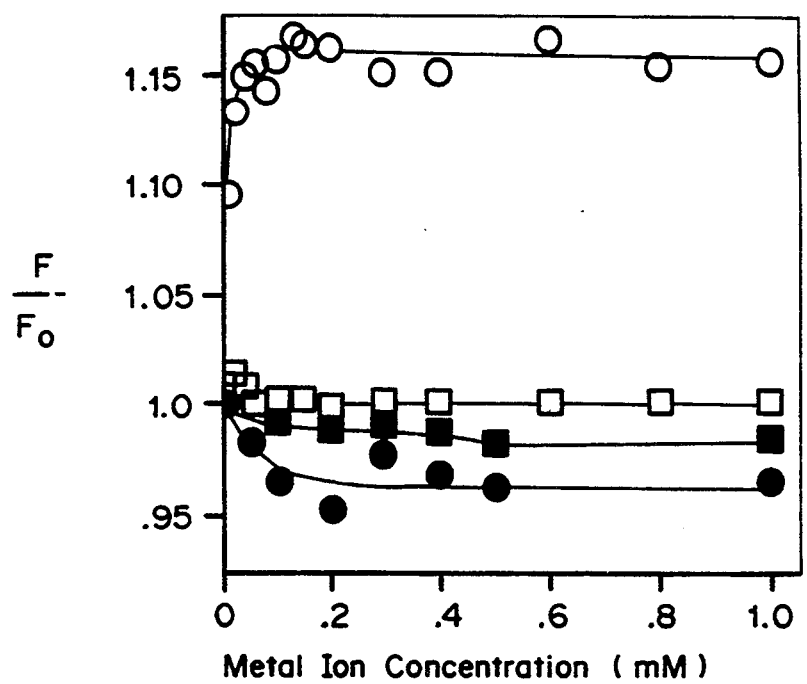
FIG. 2 is a graph of the metal ion-dependent changes in intrinsic fluorescence of HPC-4 in the presence and absence of peptide P(6-17), F/Fo versus mM metal ion concentration. 1 μM HPC-4 was titrated with metal ions in the presence or absence of 2 μM P(6-17). Tryptophan emission changes were monitored. Fo represents the HPC-4 emission peak area (± peptide) in the absence of added metal. ● and ○, $Ca^{2+}$ titration of HPC-4 or HPC-4+peptide, respectively, ■ and □, $Mg^{2+}$ titration of HPC-4 or HPC-4+ peptide, respectively.

The properties of the monoclonal antibody, HPC-4, which make it uniquely useful are as follows:

The antibody binds protein C, not activated protein C (APC), and only in the presence of calcium. Thus, when the antibody is immobilized on an affinity support, protein C can be isolated from either plasma-derived sources or from tissue culture expression systems under extremely mild conditions. This is important in maintaining the biological activity of the product and the stability of the solid support resin. Because activated protein C is not bound under any conditions, the resulting product is completely free of APC.

The antibody binds to the activation site on protein C and can therefore be used to block the formation of the anticoagulant protein APC in vivo. Because it does not bind to or inhibit APC, the in vivo inhibitory effects can be reversed by administration of APC.

The antibody binds to a defined region of the protein C molecule that is contained within residues 6 and 17 of the heavy chain, specifically E D Q V D P R L I D G K. This peptide can be immobilized directly on a solid support resin and can be used to isolate the antibody in high concentrations from mouse ascites fluid or tissue culture supernatants. This approach allows the isolation of the antibody in extremely pure form in high yield, even from very dilute solutions.

The antibody can be removed from the solid support peptide either by the removal of calcium ions, if desired, or by 1.5M guanidine, which does not affect the function of the purified monoclonal antibody. This may be significant, as guanidine is recognized as a legitimate viral deactivation agent by regulatory agencies. After elution or treatment with this agent, the antibody will not contain any live virus which may be present either in the ascites fluid derived from the mice used to produce the monoclonal antibody or culture supernatants, if tissue culture of the hybridoma is used. Accordingly, virus will not be introduced into the protein C product from the antibody used to prepare it.

The antibody recognizes protein C of human, pig and canine origin, but not bovine origin. Hence protein C present in the fetal calf serum which may be used to grow cells producing protein C through recombinant technology will not contaminate the human protein C product.

The monoclonal antibody of the present invention is secreted by Hybridoma HPC-4, which was produced as follows:

Monoclonal Antibody Production

BALB/c mice were injected intraperitoneally with 50–100 μg of purified human Protein C (HuPC) in complete Freund's adjuvant. The mice were again immunized after 3 weeks with HuPC emulsified in incomplete Freund's adjuvant and after 6 weeks with HuPC in TBS (0.1M NaCl 0.02M Tris-HCl pH 7.5). Four days later, spleen cells were fused with the mouse myeloma cell line P3X63AG8-653 using 35% polyethylene glycol 1450, using standard techniques, as described by Laurell, M., K. Ikeda, S. Lindgren, J. Stenflo, *FEBS Letters* 191, 75–81 (1985); Wakabayashi, K., Y. Sakata, N. Aoki, *J. Biol. Chem.* 261, 11097–11105 (1986); Borrebaeck, C. A. K., M. E. Etzler, *J. Biol. Chem.* 256, 4723–4725 (1981); Kohler, G., C. Milstein, *Nature* 256, 495–497 (1975).

Cells were grown in HAT medium to select for hybridomas. After four weeks, supernatants from fused cells were screened for antibody production by solid-phase enzyme-linked immunoadsorbent assay in the presence and absence of 5 mM $Ca^{2+}$.

Culture supernatants were diluted 1:4 into buffer containing either 5 mM $CaCl_2$ or 5 mM EDTA for assay. All reagents (antigen, wash buffers, detection antibodies) contained the appropriate calcium or EDTA concentrations.

Positive clones of interest, as determined on the basis of reactivity with protein C, were recloned at least two times by limiting dilution onto murine peritoneal lavage feeder cells.

The BALB/c mouse is initially primed with pristane to induce ascites fluid production and, 14 days later, injected intraperitoneally with 0.1 ml of 10 mg/ml cyclophosphamide in order to immunocompromise the animal. Seventy-four hours later, $3–6 \times 10^6$ cells are injected intraperitoneally. After 7–10 days, ascites fluid is collected and HPC-4 monoclonal antibodies purified from ascites fluid. Antibody is normally present at 8–15 mg antibody/ml ascites fluid. Three different methods can be used to purify the antibody: (1) $NH_4SO_4$ fractionation followed by QAE-Sephadex chromatography; (2) affinity chromatography on human protein C Affi-Gel 15; or (3) affinity chromatography on the peptide recognized by HPC-4, E D Q V D P R L I D G K (Glu-Asp-Gln-Val-Asp-Pro-Arg-Leu-Ile-Asp-Gly-Lys).

Alternatively, selected hybridomas can be propagated in vitro in laboratory culture vessels from which the monoclonal antibodies against the selected antigen can be harvested by decantation and purified as described for the ascites fluid. The epitope affinity resin can also be used to isolate the HPC-4 from hybridoma tissue culture supernatants. The material is directly applied to the column. The antibody concentration in an exponentially growing culture is approximately 25 $\mu$g/ml.

The monoclonal antibody HPC-4 is purified from ascites fluid by $NH_4SO_4$ fractionation (ascites fluid is diluted 1:1 with water, then precipitated by addition of equal volumes of saturated $NH_4SO_4$), followed by chromatography on QAE-Sephadex Q-50 (ammonium sulfate precipitate collected by centrifugation, desalted into 0.027M Tris $PO_4$, pH 6.3, chromatographed on a column at a ratio of 1 ml resin/ml ascites, equilibrated in 0.027M Tris $PO_4$, pH 6.3, developed with a five times column volume linear gradient of 0 to 0.4M NaCl over approximately eight hours), followed by precipitation of the antibody with 50% $NH_4SO_4$ and Sephadex G200 column chromatography in 0.1M NaCl 1 mM MOPS, pH 7.5.

The antibody can also be isolated by HuPC-Affi-Gel or peptide-Affi-Gel affinity chromatography. The epitope recognized by HPC-4 is a twelve peptide sequence within the activation region on the heavy chain of the Protein C, E D Q V D P R L I D G K, or an immunologically similar sequence. The peptide is coupled to Affi-Gel 15 to give a final concentration of approximately 1.0 mg/ml. Coupling of the epitope peptide is performed in 0.1M NaCl, 0.1M MOPS, pH 7.5, at 4° C. as described by the manufacturer (Bio-Rad, Richmond, Calif.). The Affi-Gel is washed with ice cold water immediately before use to remove the organic solvent. The epitope peptide is prepared at a concentration of 1-2 mg/ml in 0.1M NaCl, 0.1M MOPS, pH 7.5, and mixed with sufficient Affi-Gel 15 to give a final ratio of peptide to gel of 1 mg/ml. The peptide and the gel are mixed overnight (12-18 h) on a gentle rocker to couple the peptide to the gel. After the coupling reaction is completed, the resin is poured into a glass column, and washed with 0.1M NaCl 0.01M MOPS, pH 7.5. 100 ml of resin has a capacity of at least 1.5 grams of HPC-4.

Human protein C can be coupled to the Affi-Gel by the same method. Three to five mg protein C/ml of the buffer described above is mixed with sufficient Affi-Gel 15 to give a final ratio of human protein C to gel of 3-5 mg protein/ml of gel.

The desalted ammonium sulfate fraction from the ascites is loaded onto the epitope affinity column, and the column is washed with at least 4 column volumes of 0.4M NaCl, 0.02M Tris HCl, 1 mM $CaCl_2$, pH 7.5. The HPC-4 is then eluted from the column in one of the following ways: (1) 2M NaCl, 0.02M Tris HCl, 2 mM EDTA; (2) 2M NaCl, 1.5M guanidine HCl, 0.02M Tris HCl, 2 mM EDTA. The advantage of the latter is that the protein elutes as a much sharper peak, with concentrations of greater 25 mg/ml when 200 ml of ascites is applied to a 100 ml column of resin. The antibody retains greater than 95% of the capacity to bind to the epitope after elution under these conditions. HPC-4 is then either dialyzed or desalted into the appropriate buffer for further applications. No contaminants of the HPC-4 are detectable by SDS gel electrophoresis. Additional HPC-4 can be obtained by applying the breakthrough material back to the column if the column is overloaded above its capacity.

The HPC-4 antibody is stable for at least 2 hours at 22 degrees C. to guanidine to concentrations of at least 2.6M or 2M potassium thiocyanate and retains greater than 95% of the capacity to bind to the epitope after treatment under these conditions. Treatment with either of these reagents, after elution from the peptide affinity column, guarantees that any viral agents which may be present in the starting antibody containing solutions are inactivated, and that the final protein C product is not contaminated with virus originating from the antibody used to prepare it.

The hybridoma cell line which secretes the monoclonal antibody of the present invention is designated as HPC-4, and was deposited with the American Type Culture Collection, 12301 Parklawn Drive, Rockville, Md., 20852 on Nov. 2, 1988, and has been assigned ATCC No. HB 9892. This deposit is available to the public upon the grant of a patent. However, it should be understood that the availability of a deposit does not constitute a license to practice the invention in derogation of patent rights granted by governmental action.

Coupling of Protein C Monoclonal Antibody to Resin

Coupling of the antibody is performed in 0.1M NaCl, 0.1M MOPS, pH 7.5, at 4° C. as described by the manufacturer (Bio-Rad, Richmond, Calif.). The Affi-Gel is washed with ice cold water immediately before use to remove the organic solvent. HPC-4 is prepared at a concentration of 3-5 mg/ml in 0.1M NaCl, 0.1M MOPS, pH 7.5, and mixed with sufficient Affi-Gel 10 to give a final ratio of HPC-4 to gel of 5 mg/ml. Antibody and the gel are mixed overnight (12-18 h) on a gentle rocker to allow the coupling reaction. Usually greater than 90% of the antibody is bound. After the coupling reaction is completed, the resin is poured into a glass column, and washed with 0.1M NaCl 0.01M MOPS, pH 7.5. The resin is stable at 4° C. under these conditions for at least one year.

Characterization of the Monoclonal Antibody

A detailed analysis of the properties of the HPC-4 monoclonal is presented in Stearns, et al., "The Interaction of a $Ca^{2+}$-Dependent Monoclonal Antibody with the Protein C Activation Peptide Region," *J. Biol. Chem.* 263, 826–832 (1988). The HPC-4 monoclonal antibodies produced as described above are directed against a peptide sequence present in the activation region of the heavy chain of Protein C and $Ca^{2+}$. The antibody appears to have at least one metal ion binding site in addition to the peptide binding site. The peptide binding activity is responsive to, or "dependent on", binding at the metal ion binding site. The metal ion binding site is capable of binding to a divalent metal cation such as calcium, or a metal having a similar ionic radius and coordination properties such as $Tb^{3+}$.

When calcium binds to the metal ion binding site, the monoclonal antibody becomes significantly more receptive to binding to the peptide. When a metal ion is not bound to the metal ion binding site of the monoclonal antibody, the antigen binding site is relatively unreceptive to binding the antigen. Accordingly, antibody-antigen binding may be controlled by varying the metal ion concentration in the media surrounding the antibody. This characteristic of the monoclonal antibody has a number of advantages, as described below.

Binding of HPC-4 to protein C is controlled by the presence of calcium ions at the calcium ion binding site on both HPC-4 and protein C. To determine which portion of the human protein C (HuPC) contained the HPC-4 binding site, HuPC was reduced and carboxymethylated (RCM) to produce the RCM-heavy and RCM-light chains, using the method of Esmon, et al., *J. Biol. Chem.* 258, 554–556 (1983). The chains were dialyzed against 0.1M NaCl, 0.02M Tris HCl, 2 mM $CaCl_2$, pH 7.5, and applied to an HPC-4-Affi-Gel 10 column (1.5×18 cm, 0.2 ml/min, 2 ml fractions) equilibrated in the same buffer. Bound protein was eluted with the same buffer except that 2 mM EDTA was used instead of the 2 mM $CaCl_2$. The protein-containing factions were analyzed by 10% sodium dodecyl sulfate polyacrylamide gel electrophoresis.

The results demonstrated that the light chain of protein C, which is the chain of protein C that binds calcium, was not retained by the column and the heavy chain, which itself is unable to bind calcium, was retained and eluted by the EDTA containing buffer.

The role of the activation peptide region was examined by affinity chromatography on an HPC-4 Affi-Gel 10 column. HuPC and the RCM heavy chain, in a solution of 0.1M NaCl 2 mM $CaCl_2$ 0.1M MOPS, pH 7.5, were diluted to 0.2 absorbance unit/ml and 1 ml samples were applied to an HPC-4-Affi-Gel 10 column (0.5 cm×6 cm) equilibrated in the same buffer. Bound protein was eluted with 0.1M NaCl 2 mM EDTA 0.1 M MOPS pH 7.5 in 0.7 ml fractions. Fractions 23–25 of HuPC or the RCM heavy chain eluted were pooled, and the activation peptide was released by thrombin proteolysis (10%, w/w, 4 h, 37° C.). Excess antithrombin III was added to stop the reaction; the solution was recalcified to 5 mM $CaCl_2$ and applied to the same column. Recovery of proteins for each chromatogram was greater than 98% based on recovery of $A_{280}$ absorbing material.

These results showed that the HPC-4 binding site on protein C was at or near the activation site, that HuPC bound to the antibody column in a $Ca^{2+}$-dependent manner, and that, following activation to APC, HuPC no longer bound to HPC-4. The RCM heavy chain also bound to the HPC-4 column in the presence of $Ca^{2+}$ and could be eluted with EDTA. When the eluate was treated with thrombin to release the activation peptide and reapplied to the HPC-4 column, the RCM-heavy chain no longer bound to HPC-4.

The $Ca^{2+}$ dependence of HPC-4-antigen binding was examined by incubating $^{125}I$-labeled antigens: RCM heavy chain, HuPC and HuPC without gamma-carboxyglutamic acid domain (HuGDPC) with HPC-4 immobilized on Immunobeads (Bio-rad). The HPC-4 coupled to immunobeads was incubated overnight at 4° C. in TBS 0.1% gelatin 1 mM EDTA, pH 7.5, and then washed extensively with TBS 0.1% gelatin, pH 7.5 (Chelex-treated). The radiolabeled proteins were added to 100 μl of HPC-4-coupled beads with increasing concentrations of $Ca^{2+}$ in TBS 0.1% gelatin, pH 7.5. Total volume was 200 μl. The solutions were incubated with mixing for 2 h, at 25° C., and washed with gelatin buffer containing the appropriate amount of $Ca^{2+}$, and the beads counted in an NE 1600 gamma counter (Nuclear Enterprises, Ltd. ). Control samples included solutions with no added $Ca^{2+}$ and 1 mM EDTA, respectively.

Final antigen concentrations ranged from 0.04 to 0.1 μM, which were sufficiently low to ensure an excess of antibody binding sites. Baseline counts/minute determined in the presence of 1 mM EDTA (5–15% of total counts added) were subtracted from the bound total counts/minute.

Maximal binding of the $^{125}I$-labeled RCM heavy chain was 80–90% of the total amount added and 60–70% of the added $^{125}I$-labeled HuPC or HUGDPC. The $Ca^{2+}$ concentration resulting in half-maximal binding to HPC-4 was approximately 36 ($\pm5$) μM for the RCM heavy chain, 110 ($\pm29$) μM for HuGDPC and 205 ($\pm23$) μM HuPC.

No high affinity $Ca^{2+}$-binding site was detected in either protein when equilibrium dialysis experiments with $^{45}Ca^{2+}$ were performed with HPC-4 (50 μM) or RCM heavy chain (35 μM), However, when dialyzed together (30 μM RCM heavy chain, 15 μM HPC-4), the results indicated between 2 and 3 mol of $Ca^{2+}$ bound per mol of complex at 2 mM $Ca^{2+}$, assuming a 2:1 stoichiometry of RCM heavy chain to HPC-4 in the complex.

Since the activation peptide region was required for antibody binding, three overlapping synthetic peptides were prepared to cover this area:

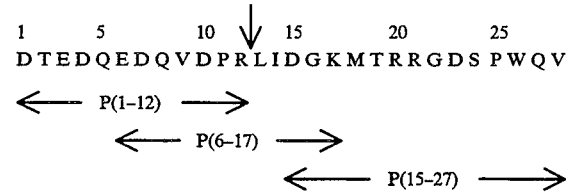

wherein D is aspartic acid, T is threonine, E is glutamic acid, Q is glutamine, V is valine, P is proline, R is arginine, L is leucine, I is isoleucine, G is glycine, K is lysine, M is methionine, S is serine and W is tryptophan. The arrow indicates the thrombin cleavage site.

The synthetic peptides were prepared by solid-phase synthesis performed with an Applied Biosystems 430A peptide synthesizer using t-butoxycarbonyl chemistry by Dr. Kenneth Jackson, St. Francis Hospital, Tulsa Medical Research Institute, at the University of Oklahoma Health Science Center, Oklahoma City. Peptides were cleaved by treatment with anhydrous hydrogen fluoride. Purity of the peptides as assessed by reverse-phase high pressure liquid chromatography was >90%. Molecular weight of the peptides was estimated by summation of the individual anhydrous amino acid molecular weights with correction for peptide bond formation. Peptide concentrations were estimated by reference to the absorbance at 220 nm of 1 mM peptide solutions in purified water.

The three peptides were assayed for their effect on $^{125}I$-labeled HPC-4 binding to solid-phase HuPC, wherein the HuPC was coated on wells of a microtiter plate. P(1-12) did not inhibit HPC-4 binding to HuPC; P(15-27) inhibited HPC-4 binding only about 30%; but P(6-17) inhibited the binding of HPC-4 to HuPC with half-maximal inhibition occurring at approximately 0.5 μM peptide.

HPC-4 interaction with the three synthetic peptides was also studied by monitoring intrinsic protein fluorescence in the presence and absence of $Ca^{2+}$, according to the methods of Velick, et al., *Proc. Nat. Acad. Sci.*

USA 46, 1470–1482 (1960) and Steward, et al., *Antibody Affinity: Thermodynamic Aspects and Biological Significance*, 76–77 (1983).

For the intrinsic fluorescence studies, 1 μM HPC-4 antibody in TBS, pH 7.5 (Chelex-treated), in the presence or absence of 2 μM P(6–17), was titrated with $CaCl_2$ or $MgCl_2$ diluted in the same buffer. HPC-4 titrated with the synthetic peptide P(1–12), P(6–17), or P(15–27) was at a final concentration of 5 μM, in a solution containing either 1 mM EDTA or 1 mM $CaCl_2$ before addition of peptides. The emission intensity (305–400 nm) was recorded 5 min after each addition of titrant. Under all experimental conditions, sample dilution due to addition of titrant contributed <4% of the observed change in the signal.

Since the peptide that binds does not contain aromatic amino acids, any changes in intrinsic fluorescence observed are directly attributable to changes in the antibody resulting from peptide binding. The intrinsic fluorescence of HPC-4 increased when titrated with P(6–17) in the presence of 1 mM $Ca^{2+}$, reaching a maximum by the expected 2:1 ratio of peptide to antibody. In 1 mM EDTA, the fluorescence also increased, but this required higher peptide concentrations. Synthetic peptides P(1–12) and P(15–27) did not significantly change the HPC-4 fluorescence in the presence of $Ca^{2+}$.

The $Ca^{2+}$ dependence of HPC-4-P(6–17) binding was also studied using fluorescence methods. The intrinsic fluorescence of HPC-4 in the presence of P(6–17) increased when titrated with $Ca^{2+}$ with the half-maximal change occurring at 6.5±1.2 μM $Ca^{2+}$. 1 μM HPC-4 was titrated with metal ions in the presence or absence of 2 μM P(6–17). Tryptophan emission changes were monitored as previously described. $Mg^{2+}$ had no effect on HPC-4 intrinsic fluorescence in the presence or absence of the peptide. $Ca^{2+}$ titration of the antibody in the absence of peptide showed only 5% quenching of the intrinsic fluorescence, indicating a possible low affinity $Ca^{2+}$ interaction with the antibody.

$Tb^{3+}$ was used to study the $Ca^{2+}$ binding site since $Tb^{3+}$ fluorescence emission becomes greatly enhanced when it binds to a site on a protein close enough to a tryptophan or tyrosine residue to allow efficient singlet-singlet transfer. P(6–17) does not contain donor aromatic amino acids for enhanced fluorescence, while HPC-4 does. 1 μM HPC-4 in 0.1M MES 0.1% gelatin 0.02% $NaN_3$, pH 6.0 was titrated with $Tb^{3+}$ in the presence or absence of 4 μM P(6–17). HPC-4 tryptophan was excited at 285 nm using an SB 300 UV bandpass filter (Oriel) in the excitation path. $Tb^{3+}$ ion emission intensity was recorded at 2-nm intervals and integrated from 538 to 552 nm. Contributions from light scattering were measured as the harmonic of the excitation wavelength recorded at 570–580 nm. For each $Tb^{3+}$ concentration, the emission intensity of the solvent blank titrated in parallel with the sample was subtracted from that of the protein solution to give only the protein-dependent $Tb^{3+}$ fluorescence.

Titration of HPC-4 with $Tb^{3+}$ resulted in increased $Tb^{3+}$ fluorescence that was half-maximal at a free $Tb^{3+}$ concentration of 34±11 μM. $Tb^{3+}$ titration of HPC-4 in the presence of P(6–17) also resulted in enhanced $Tb^{3+}$ fluorescence, but the half-maximal free $Tb^{3+}$ concentration decreased to 2±0.9 μM. Control experiments in which the peptide was titrated under the same conditions showed no enhancement of $Tb^{3+}$ fluorescence, thus showing that the peptide alone was not responsible for changes in fluorescence. The 17-fold increase in affinity for $Tb^{3+}$ by the peptide-HPC-4 complex demonstrates the transformation of a low affinity metal ion binding site in HPC-4 to a high affinity site.

These results were confirmed with respect to $Ca^{2+}$ binding to the antibody peptide complex using the Hummel-Dreyer gel filtration technique, *Biochem. Biophys. Act* 63, 530–532 (1962). P(6–17), HPC-4, and mixtures thereof were applied to the column, and their ability to bind $Ca^{2+}$ determined. P(6–17) did not bind $Ca^{2+}$. HPC-4 and a 3.5 fold molar excess of P(6–17) showed a $Ca^{2+}$ binding increase to 1.76 mol of $Ca^{2+}$/mol of HPC-4. $Mg^{2+}$ had no effect on $Ca^{2+}$ binding by the HPC-4/P(6–17) complex (1.41 and 1.52 mol of $Ca^{2+}$/mol of HPC-4 in 0.01 mM $Ca^{2+}$ or 0.02 mM $Ca^{2+}$, respectively).

The present invention includes an immunologically active fragment (epitope) of protein C which binds the antibody HPC-4, encompassing at least a portion of the amino acid sequence glutamic acid-aspartic acid-glutamine-valine-aspartic acid-proline-arginine-leucine-isoleucine-aspartic acid-glycine-lysine, as shown in FIG. 1 in residues 6 to 17 of the heavy chain.

As described above, the peptide can be used in the isolation and purification of HPC-4 by affinity chromatography. In a similar manner, the peptide can be used to temporarily "protect" the binding site during the process in which the antibody is bound to the chromatography substrate, to insure that the maximum amount of bound antibody is available for binding to the protein to be isolated. The reactive groups of the peptide which are capable of reacting with the chromatography substrate (amino terminal, lysine side chain), which are not required for recognition by HPC-4, are first blocked by reaction of the peptide with acetic anhydride using standard methods known to those skilled in the art. After the HPC-4 is coupled to the resin, the peptide bound in the antigen binding site of the antibody is removed by washing the resin with 1.5M Guanidine HCl, 2 mM EDTA, 0.02M Tris HCl, pH 7.5.

The antibody and peptide can be bound to a variety of substrates, for use in purification and isolation of Protein C and the antibody, respectively, including agarose, acrylamide and other types of conventional chromatographic resins, filters, etc. These materials are known to those skilled in the art, as are the methods for attaching the protein to them. The selection of the material will depend in large part on the scale of the purification or the sample to be analyzed, as well as biocompatibility and government agency approval where the end-product is for pharmaceutical use. Similarly, methods and means for labeling the antibody for use as a diagnostic are known to those skilled in the art, including labelling with a radioactive, fluorescent, luminescent, or enzymatic molecule.

Antigen Recovery Using Immobilized Antibodies Having Metal-Dependent Antigen Binding Sites The monoclonal antibody of the present invention has been demonstrated to have an antigen binding site and at least one metal ion binding site. Occupancy of the ion binding site is required for high affinity binding of the antigen. The amino acid sequence of the metal ion binding region of the antibody can be determined, or the gene for the variable region determined from cloning and cDNA sequencing. This segment of the cDNA can then be inserted into genes encoding other proteins, especially antibodies, to confer metal binding capability on the resulting protein. These chimeric antibodies can then be used for isolating other molecules that do not themselves undergo metal dependent conformational changes. This is a great advantage in protein purification, as finding a monoclonal antibody which has gentle elution conditions is often extremely difficult, leading to an inability to elute the proteins of interest in functional form. As a result, the potential of monoclonal antibodies in protein purification has not been fully realized. Antibodies that bind to an antigen in a metal-dependent fashion because of the antibody's ability to bind metal, rather than the requirement that the antigen itself undergo metal dependent conformational changes, can be used in affinity chromatography under very gentle conditions, the antigen being eluted with a chelating or metal containing solution.

The metal binding region of HPC-4 can be localized using limited proteolysis techniques to produce small fragments of the antibody. The fragment capable of binding metal ions can be identified by its ability to enhance $Tb^{3+}$ fluorescence, as this ion has sufficient affinity for the antibody in the absence of antigen to detect its binding. Fab, Fab' and Fc fragments of the antibody can be made by standard techniques, using pepsin and papain digestion, by those skilled in the art. Smaller fragments can be produced from the appropriate portion of the antibody by CNBr cleavage, as well as by digestion with other proteolytic enzymes, as described in Kurosawa, S., et al, *J. Biol. Chem.*, 263:5993–5996, 1988; Ohlin, A-K and J. Stenflo, *J. Biol. Chem.*, 263:7411–4717, 1988; Stearns, D. J., et al, *J. Biol. Chem.*, "Micro-thrombomodulin; Residues 310–486 from the epidermal growth factor precursor-homology domain of thrombomodulin will accelerate protein C activation" (in press 1989); until the smallest fragment which retains ion binding function is obtained.

HPC-4 cDNA can be cloned and sequenced by methods known to those skilled in the art. cDNA can be prepared from hybridoma cell line HPC-4 (ATCC number 9892) and a lambda gt11 expression library constructed (T. V. Huynh, et al in DNA cloning: a practical approach, vol. 1, (D. M. Glover, ed.), IRL Press, Oxford, 1985, pp. 49–78.) The library can be screened using affinity purified goat anti-HPC-4 antibody. Appropriate clones are then expanded, the eDNA excised and inserted into M13 for standard DNA sequencing (M13 cloning and sequencing handbook, Amersham; Messing, J., "New M13 vectors for cloning," *Methods in Enzymology—Recombinant DNA techniques*, 101,part C: 20–78, 1983).

In addition, fragments expressed by clones that react positively with the anti-HPC-4 can also be purified and tested for the ability to bind $Tb^{3+}$, allowing an additional method for finding the region of interest in the HPC-4 molecule. Once the fragment of the DNA which corresponds to the appropriate ion binding fragment of the HPC-4 antibody gene is located, the appropriate restriction enzyme, such as EcoR1, is used to excise this fragment. Methods for constructing chimeric genes have been disclosed by, for example, Kobilka, B. K., et al, "Chimeric $\alpha_2$-, $\beta_2$-Adrenergic Receptors: Delineation of Domains Involved in Effector Coupling and Ligand Binding Specificity" Science 240:1310–1316, 1988; Verhoeyen, M., C. Milstein, G. Winter, "Reshaping Human Antibodies: Grafting an Antilysozyme Activity," Science, 239:1534–1536, 1988; Riechmann, L., M. Clark, H. Waldmann, G. Winter, "Reshaping human antibodies for therapy," Nature, 332:323–327, 1988). The target DNA, containing the gene for the monoclonal antibody of interest will be treated similarly to the source DNA with restriction enzyme so that the space for the insertion of the cDNA fragment is available. Linkers with compatible ends are then ligated to the insert (e.g., SalI) and the ligation performed. The chimeric cDNA can then be cloned into an appropriate expression vector, such as Baculovirus according to the procedures described in Summers, M. D. and G. E. Smith, "A manual of methods for Baculovirus vectors and insect cell culture procedures", Texas Agricultural Experimental Station (1987). Expression of the recombinant gene can be achieved by the methods described therein. Screening for the desired product can be achieved by ELISA assay wherein released protein is tested for its ability to recognize the antigen for which the target immunoglobulin was specific in a metal dependent manner. Whether the presence or absence of metal ion is required for recognition of the antigen will most likely depend on the particular antibody-antigen pair.

In the event that the metal binding region of HPC-4 does not reside in a single stretch of amino acids, for example, if segments of both the heavy and light chain of the immunoglobulin contribute to this site, it will be necessary to repeat the procedure for each such segment, as described by Verhoeyen, M., et al, *Science*, 1988; Riechmann, L., et al, *Nature*, 1988). It will be recognized by those skilled in the art that the present invention is not limited to the use of particular nucleases, vectors or expression systems at any point in the procedure disclosed above, and includes any combination which ultimately leads to the production of functional antibody able to bind the antigen of interest in a metal dependent manner, due to the insertion of the appropriate peptide sequence(s) from HPC-4.

Therapeutic Uses of HPC-4

The coagulant and anticoagulant systems in mammals provide a delicate check and balance system which maintains blood in its proper fluid state. Alteration of any single element in this system can have an enormous impact on the ability of the mammal to maintain hemostasis.

The protein C system is an anticoagulant, regulatory system which inhibits blood coagulation and stimulates fibrinolysis. This system is activated by thrombin, an enzyme which converts fibrinogen to fibrin in the coagulative process. Free or excess thrombin binds with thrombomodulin, a protein on endothelial cells. The thrombin-thrombomodulin complex decreases the ability of thrombin to catalyze clot formation and converts thrombin into a potent protein C activator. Activated Protein C in turn acts in combination with Protein S and a membrane surface to inactivate factor Va and factor VIIIa by limited proteolysis. The inactivated factor Va loses the ability to interact effectively with the enzyme factor Xa or the substrate prothrombin.

Addition of an antibody to Protein C, an antibody to thrombomodulin, an antibody to Protein S, or C4b binding protein, which binds Protein S to thereby inactivate it as a cofactor, in an appropriate form, can be used to promote clotting in individuals where it is desirable to do so. Patients having FVIII inhibitors are representative of this group of patients. By preventing the factor Va from being inactivated, coagulation proceeds even in the relative absence of factor VIII.

The effect of administering these inhibitors of the Protein C anticoagulation system can be reversed by administration of excess amounts of Activated Protein C or Protein S, depending on the agent used to block the pathway. The appropriate amount is based on calculations relating to the relative molar amounts of the proteins present in the blood.

The feasibility of this approach to produce a hypercoaguable state has been demonstrated by the administration of HPC-4 to baboons (Taylor, et al, *J. Clin. Invest.*, 79, 918-925 (1987). When HPC-4 was present, the animals developed a massive coagulation response, characterized by total fibrinogen consumption, to the infusion of low levels of bacteria. They did not develop this response in the absence of the antibody. Virtually identical results are obtained when C4bBP levels are elevated to approximately 1 mg/ml plasma. While these responses are detrimental to the animals, they illustrate that either method will enhance the coagulation system. This is beneficial in situations where normal hemostasis is impaired.

This method can also be applied in the treatment of other clotting factor deficiency states, including thrombocytopenia, for example, as induced by heparin or radiation therapy, liver disease and hemorrhagic stroke, both acutely and to minimize rebleeding after the acute incident.

HPC-4 can also be used to induce microvascular clotting in a solid tumor bed. In a canine solid tumor model, this has been found to greatly impede growth of the tumor. The combination of this antibody and/or the other agents indicated above which are capable of blocking the function of the protein C anticoagulant pathway with other treatments presently in use, such as tumor necrosis factor or radiation, may lead to more efficacious treatment of solid tumors.

Pharmaceutically acceptable carriers for administration of these agents include sterile normal saline at physiological pH. In the preferred method of administration, the agent is injected into the subject, most preferably, intravenously. Preferred dosages are between about 5 and about 20 μg HPC-4/ml plasma, which is sufficient to block greater than 90% of the endogenous protein C.

EXAMPLE 1

Large Scale, Rapid Isolation of Protein C from Plasma

Rapid isolation of protein C was accomplished following the flow diagram illustrated below. Briefly, protein C and the other vitamin K-dependent proteins are batch adsorbed onto QAE Sephadex Q50 (30 g swollen in 0.1M NaCl, 0.02 Tris HCl pH 7.5) from 30 liters of human plasma diluted 1:1 with 0.02M Tris HCl, pH 7.5, heparin (1 U/ml final volume) and benzamidine HCl (10 mM final volume) for 1 h at room temperature, allowed to settle for 30-60 min and the supernatant siphoned off. The Sephadex is packed in a 10×60 cm column, washed with 1 l 0.15M NaCl, 0.02M Tris HCl, 10 mM benzamidine HCl, pH 7.5 before eluting the protein C with 0.5M NaCl in the same buffer. The volume of the pool is decreased to approximately 600 ml. To this volume is added Heparin to 10 U/ml, $Ca^{2+}$ to 10 mM, DFP to 1 mM and approximately 100 ml HPC-4 Affi-Gel 10. This mixture is stirred for 1 h, allowed to settle, packed into a 2.5×20 cm column, washed with 1 l 0.5M NaCl, 0.02M Tris HCl, 5 mM benzamidine HCl, 2 mM $CaCl_2$, pH 7.5, then 100 ml 0.1M NaCl, 0.02 Tris HCl, 2 mM $CaCl_2$, pH 7.5, before eluting protein C with the same buffer containing 2 mM EDTA instead of $Ca^{2+}$.

Contamination by serum amyloid P, a protein which binds Sephadex in the presence of $Ca^{2+}$, is removed by ion exchange chromatography on QAE Sephadex Q50. The column (0.9×30 cm) is developed in a linear gradient from 0.1 to 0.6M NaCl in 0.02M Tris HCl, pH 7.5. Protein C elutes as the last peak from the column. This may be confirmed by SDS gel electrophoresis, protein C antigen and protein C functional assays. This preparation yields single chain and two chain protein C in the approximate proportions found in human plasma.

| PROTEIN C PURIFICATION |
| --- |
| Batch adsorption of diluted |
| Heparinized plasma on QAE Sephadex |
| Wash with buffered 0.15 M NaCl |
| Elute with buffered 0.5 M NaCl |
| Recalcify and batch adsorb with HPC-4 |
| Wash with $Ca^{2+}$ containing buffer |
| Elute with EDTA containing buffer |

When commercially prepared vitamin K-dependent plasma protein concentrates, such as Konyne (Cutter Labs), Proplex (Hyland) or FEIBA (IMMUNO, Austria), are used instead of plasma, the concentrates are reconstituted in a buffer compatible with HPC-4 binding of protein C (i.e., one buffered between pH 6 and pH 7.5 containing 2 mM $CaCl_2$, anticoagulants such as heparin at 5-10 units/ml and antithrombin III (10-100 (μg/ml) and protease inhibitors such as benzamidine and DFP at 1 mM each) and directly applied to the HPC-4-Affi-Gel 10 resin either in batch or in a column. Washing and elution conditions used are the same as those detailed above. QAE chromatography after elution of the protein C from the HPC-4 resin is only required if serum amyloid P is present in the material applied to the affinity resin.

When supernatant from tissue culture cells genetically engineered to produce human protein C is used instead of plasma or concentrate, it can either be directly mixed with the HPC-4 affinity resin after the addition of 2 mM $CaCl_2$ and protease inhibitors or after concentration and resuspension in a buffer compatible with protein C binding to the HPC-4, such as that detailed above. The supernatant can be concentrated by means of 50% $NH_4SO_4$ precipitation or ion exchange, as described previously with reference to plasma. The usual yield of protein C is 0.04 mg protein C/mg antibody.

EXAMPLE 2

Use of HPC-4 as a Diagnostic for Protein C

HPC-4 can be used to analyze protein C in human plasma. Protein C can be quantitatively adsorbed and reproducibly eluted from immobilized HPC-4. The resultant protein C can be analyzed for functional properties. This is useful for the unambiguous demonstration of protein C deficiency in selected patients with recurrent thrombosis and abnormal protein C molecules. Examples of the use of Protein C antibodies for diagnostic purposes are illustrated in D'Angelo, S. V., et al, *J. Clin. Invest.*, 77: 416-425, 1986 and Faioni, E., et al, *Blood*, 71:940-946, 1988.

In addition, the antibody can be labelled with a tracer, such as $^{125}$I using Enzymobeads (Bio-Rad), biotin (Shattil, S, et al, *Blood*, 70:307-315, 1987), or other tag as appropriate and known to those skilled in the art for the purpose of developing routine immunological assays for use in clinical laboratories, such as enzyme linked immunoassay (ELISA) or radioimmunoassay (RIA) for the purposes of determining antigenic levels of protein C in clinical plasma samples.

However, it should be noted that although the description of methods using antibodies has been disclosed previously, the monoclonal antibody of this invention has not been publicly available.

We claim:

1. A method for isolating the zymogen of Protein C or the heavy chain thereof comprising
   (1) providing an immobilized calcium dependent monoclonal antibody specific for an epitope in the activation peptide region of the heavy chain of Protein C and calcium, wherein the antibody is produced by the hybridoma cell line HPC-4 deposited with the American Type Culture Collection, Rockville, Md., on Nov. 2, 1988, and assigned accession No. HB 9892;
   (2) providing a solution containing calcium and the zymogen of Protein C or the heavy chain thereof to be isolated under conditions that allow the antibody to bind the activation peptide region in combination with binding calcium; and
   (3) eluting the zymogen of Protein C or heavy chain thereof from the antibody by removing calcium.

2. The method of claim 1 wherein the antibody is immobilized on a solid substrate selected from the group consisting of chromatographic resins and filters.

* * * * *